United States Patent
Choi et al.

(10) Patent No.: US 12,144,838 B2
(45) Date of Patent: Nov. 19, 2024

(54) **COMPOSITION FOR PREVENTING, ALLEVIATING OR TREATING NEURODEGENERATIVE DISEASES, COMPRISING *PEDIOCOCCUS INOPINATUS***

(71) Applicant: KOREA FOOD RESEARCH INSTITUTE, Jeollabuk-do (KR)

(72) Inventors: Hak Jong Choi, Gwangju (KR); Nam Hee Kim, Jeollanam-do (KR); Hyo Kyeong Park, Gwangju (KR)

(73) Assignee: KOREA FOOD RESEARCH INSTITUTE, Jeollabuk-do (KR)

(*) Notice: Subject to any disclaimer, the term of this patent is extended or adjusted under 35 U.S.C. 154(b) by 49 days.

(21) Appl. No.: 17/423,183

(22) PCT Filed: Jan. 15, 2020

(86) PCT No.: PCT/KR2020/000754
§ 371 (c)(1),
(2) Date: Jul. 15, 2021

(87) PCT Pub. No.: WO2020/149647
PCT Pub. Date: Jul. 23, 2020

(65) Prior Publication Data
US 2022/0125862 A1 Apr. 28, 2022

(30) Foreign Application Priority Data
Jan. 15, 2019 (KR) .......................... 10-2019-0005270

(51) Int. Cl.
*A61K 35/744* (2015.01)
*A23K 10/18* (2016.01)
(Continued)

(52) U.S. Cl.
CPC ............ *A61K 35/744* (2013.01); *A23K 10/18* (2016.05); *A23L 33/135* (2016.08); *A23L 33/40* (2016.08);
(Continued)

(58) Field of Classification Search
CPC .... A61K 35/744; A61K 35/20; A61K 35/747; A61K 35/74; A61K 2236/19;
(Continued)

(56) References Cited

U.S. PATENT DOCUMENTS

2013/0071367 A1 3/2013 Bauer
2021/0338746 A1* 11/2021 Ahmed ................... A61P 19/02

FOREIGN PATENT DOCUMENTS

KR 1020140023241 2/2014
KR 101424547 B1 * 8/2014
(Continued)

OTHER PUBLICATIONS

Fratiglioni et al, Prevention of common neurodegenerative disorders in the elderly, Exper. Gerontol., 44, 46-50, published online Jun. 24, 2008 (Year: 2008).*
(Continued)

*Primary Examiner* — Louise W Humphrey
*Assistant Examiner* — Alexander M Duryee
(74) *Attorney, Agent, or Firm* — DUANE MORRIS LLP; Gregory M. Lefkowitz; Brandon A. Chan

(57) ABSTRACT

A composition for preventing, alleviating or treating a neurodegenerative disease, which contains *Pediococcus inopinatus* as an active ingredient. The *Pediococcus inopinatus* strain can suppress neuroinflammation and can also alleviate the symptoms of ataxia in an animal model of Parkinson's disease and, thus, can be utilized for the prevention, alleviation and treatment of various neurodegenerative diseases including Parkinson's disease.

9 Claims, 3 Drawing Sheets

(51) Int. Cl.
  *A23L 33/00* (2016.01)
  *A23L 33/135* (2016.01)
  *A61K 35/20* (2006.01)
  *A61P 25/16* (2006.01)

(52) U.S. Cl.
  CPC .............. *A61K 35/20* (2013.01); *A61P 25/16* (2018.01); *A23V 2002/00* (2013.01); *A23V 2400/423* (2023.08)

(58) Field of Classification Search
  CPC ....... A23K 10/18; A23K 20/10; A23L 33/135; A23L 33/40; A23L 2/52; A61P 25/16; A61P 25/28; A23V 2002/00; A23V 2200/316; A23V 2200/322; A23Y 2280/41
  See application file for complete search history.

(56) References Cited

FOREIGN PATENT DOCUMENTS

| KR | 1020150010489 | 1/2015 |
| KR | 101617141 | 4/2016 |
| KR | 1020160050858 | 5/2016 |
| KR | 1020170032845 | 3/2017 |

OTHER PUBLICATIONS

Lopes et al. Topical application of probiotics in skin: adhesion, antimicrobial and antibiofilm in vitro assays. J Appl Microbiol. Feb. 2017;122(2):450-461.Published online Dec. 12, 2016 (Year: 2016).*
"Friedreich's Ataxia Fact Sheet", NINDS, Publication date Jun. 2018, https://www.ninds.nih.gov/friedreich-ataxia-fact-sheet, NIH Publication No. 18-NS-87 (Year: 2018).*
Fang, X. et al., "Microbial treatment: the potential application for Parkinson's disease," Neurol Sci., Jan. 2019;40 (1):51-58. doi: 10.1007/s10072-018-3641-6. Epub Nov. 10, 2018. PMID: 30415447.
Chen, W.W., et al., "Role of neuroinflammation in neurodegenerative diseases (Review)," Molecular Medicine Reports, 2016, 13: 3391-3396.
Gelgers, G., et al., "Linking Neuroinflammation and Neurodegeneration in Parkinson's Disease," Journal of Immunology Research vol. 2018, Article ID 4784268, 12 pages.
Wang, Q., et al., "Neuroinflammation in Parkinson's disease and its potential as therapeutic target," Translational Neurodegeneration (2015) 4:19.
Takata K, Kinoshita M, Okuno T, Moriya M, Kohda T, et al. (2011) "The Lactic Acid Bacterium Pediococcus acidilactici Suppresses Autoimmune Encephalomyelitis by Inducing IL-10-Producing Regulatory T Cells". PLoS One 6(11): e27644. doi:10.1371/journal.pone.0027644.
Enan, G., et al., "Classification, Antimicrobial Potential, Industrial Applications and Probiotic Capability of Lactic Acid Bacteria: A Review Article," Research Journal of Applied Sciences, 2018, 13 (12): 742-757.

* cited by examiner

COMPOSITION FOR PREVENTING, ALLEVIATING OR TREATING NEURODEGENERATIVE DISEASES, COMPRISING *PEDIOCOCCUS INOPINATUS*

CROSS-REFERENCE TO RELATED APPLICATIONS

This application is a § 371 national stage entry of International Application No. PCT/KR2020/000754, filed on Jan. 15, 2020, which claims priority to Korean Patent Application No. 10-2019-0005270, filed on Jan. 15, 2019, the entire contents of which are incorporated herein by reference.

TECHNICAL FIELD

The present disclosure relates to a composition for preventing, alleviating or treating a neurodegenerative disease, which contains *Pediococcus inopinatus*, a culture thereof, a lysate thereof, a pulverization product thereof, a fermentation product thereof or an extract thereof.

BACKGROUND ART

Neurodegenerative diseases refer to degenerative diseases occurring with aging, particularly in the brain. Neurodegenerative diseases may be classified depending on main symptoms and the affected part of the brain. Typical examples are Alzheimer's disease and Parkinson's disease. Although it is known that neurodegenerative diseases are caused by neurodegeneration due to aging and aggregation of proteins owing to genetic and environmental factors, which lead to the death of nerve cells, the exact cause is not known yet.

Parkinson's disease is the second most prevalent neurodegenerative disease after Alzheimer's disease. It is reported that about 1% of the people aged 50 years or older suffer from this disease. The main symptoms of Parkinson's disease are tremor, rigidity, slowness of movement, postural instability, etc. It is a chronic disease caused by the deficit of a neurotransmitter called dopamine in the brain. Dopamine is produced by nerve cells in the substantia nigra of the brain. The nerve cells of the substantia nigra are intricately connected to the motor cortex and other various parts of the brain. Parkinson's disease is caused by the deficit of dopamine which is a substance secreted for regulation of the function of the basal ganglia in the substantia nigra.

The main symptoms of Parkinson's disease are 1) slowness of movement (bradykinesia), 2) tremor at rest, 3) muscle rigidity, 4) loss of postural reflexes, 5) abnormally flexed posture, 6) freezing of gait, etc.

The currently available therapies for Parkinson's disease include drug therapy, surgery, physical therapy, etc. For drug therapy, drugs which boost the depleted level of dopamine in the brain, prevent or delay the destruction of nerve cells by neutralizing the imbalance in neurotransmitters caused by the deficit of dopamine and control other symptoms such as depression, etc. are generally used. For example, dopamine-replacing drugs such as L-DOPA or drugs that act on the dopamine receptor are used for the treatment of Parkinson's disease. However, these drugs are limited in that they aim only at the control of symptoms since it is difficult to regenerate the dead nerve cells and that long-term medication results in severe side effects such as involuntary movement (dyskinesia), vomiting, etc. Accordingly, development of a drug that alleviates symptoms and provides neuroprotective effect with ensured safety is imminent.

In particular, it was recently reported that the change in gut microbiota induced in patients with Parkinson's disease is pathophysiologically associated with the progress of Parkinson's disease. Moreover, it was found out that fecal microbiota transplantation (FMT) to an animal model of Parkinson's disease resulted in neuroprotective effect through regulation of neuroinflammation (non-patent document 1).

Under this background, prevention and treatment of Parkinson's disease using lactic acid bacteria are studied recently. However, lactic acid bacteria that directly affect the symptoms of ataxia of Parkinson's disease, except constipation, have not been found yet. Therefore, development of lactic acid bacteria capable of alleviating or treating the symptoms of ataxia caused by Parkinson's disease is necessary.

REFERENCES OF RELATED ART

Non-Patent Documents (Non-patent document 1) Xin Fang, Microbial treatment: the potential application for Parkinson's disease, *Neurological Sciences*, 2018.

DISCLOSURE

Technical Problem

The present disclosure is directed to providing a composition for preventing, alleviating or treating a neurodegenerative disease, which contains *Pediococcus inopinatus*, a culture thereof, a lysate thereof, a pulverization product thereof, a fermentation product thereof or an extract thereof as an active ingredient.

Technical Solution

The inventors of the present disclosure have made efforts to find a probiotic strain having therapeutic effect for neurodegenerative diseases. As a result, they have found that a *Pediococcus inopinatus* strain isolated from kimchi not only suppresses neuroinflammation but also alleviates the symptoms of ataxia in a mouse model of Parkinson's disease when administered directly.

The *Pediococcus inopinatus* strain according to the present disclosure is specifically a *Pediococcus inopinatus* strain derived from kimchi, more specifically a *Pediococcus inopinatus* WIKIM27 strain, most specifically a *Pediococcus inopinatus* WIKIM27 strain with the accession number KCCM12653P, although not being limited thereto.

The *Pediococcus inopinatus* strain of the present disclosure is a Gram-positive, facultative anaerobe which can grow under both aerobic and anaerobic conditions. It does not form spores, lacks motility and has a spherical shape.

The *Pediococcus inopinatus* strain of the present disclosure has the general probiotic effect and immune-enhancing effect of lactic acid bacteria as a probiotic. It is well known that the lactic acid bacteria in the genus *Pediococcus* have probiotic effect and immune-enhancing effect.

In the present disclosure, the 'probiotics' are understood as live organisms that provide health benefits by improving the microbial environment in the intestine of animals including human. The probiotics are live organisms having probiotic activity and may favorably affect the gut microbiota of the host when consumed as single or multiple strains in the form of dried or fermented preparations.

In a specific exemplary embodiment, the present disclosure provides a composition containing *Pediococcus inopinatus*, a culture thereof, a lysate thereof, a pulverization product thereof, a fermentation product thereof or an extract thereof.

The *Pediococcus inopinatus* contained in the composition according to the present disclosure may be in the form of a live probiotic or a killed probiotic, and may also be dried or freeze-dried. Suitable types of lactic acid bacteria for various compositions and methods for preparing the same are well known to those skilled in the art. For example, *Pediococcus inopinatus* may be cultured using a known liquid or solid medium, the strain may be cultured together with additional ingredients and then fermented, the strain may be extracted with an organic solvent, or the cell membrane of the strain may be lysed or homogenized (lysate), although not being limited thereto.

In a specific exemplary embodiment, the composition may be a composition containing a *Pediococcus inopinatus* WIKIM27 (accession number KCCM12653P) strain.

In another specific exemplary embodiment, the composition may be a composition containing a live or killed *Pediococcus inopinatus* WIKIM27 strain.

In another specific exemplary embodiment, the composition may be a composition containing a culture, lysate, fermentation product or extract of a *Pediococcus inopinatus* WIKIM27 strain.

The present disclosure provides a probiotic composition containing *Pediococcus inopinatus*, a culture thereof, a lysate thereof, a pulverization product thereof, a fermentation product thereof or an extract thereof. The probiotic composition according to the present disclosure may be used to prevent, treat or alleviate the gastrointestinal diseases of an animal including human. Specifically, the animal includes livestock such as cow, horse and pig. The 'gastrointestinal diseases' include viral infection and inflammatory bowel disease. For example, infectious diarrhea, gastroenteritis, inflammatory bowel disease, neurogenic colitis syndrome, microbial hypergrowth in the small intestine, enterokinetic diarrhea, etc. caused by pathogenic microorganisms (*E. coli, Salmonella, Clostridium*, etc.) are included, although not being limited thereto.

Specifically, the probiotic composition according to the present disclosure may be administered orally. Although the administration dosage may vary depending on the particular gastrointestinal disease, severity of the disease, age, sex, ethnic group, purpose of treatment or prevention, etc., 10 million to 100 billion bacteria may be administered daily in general for an adult.

The present disclosure provides a composition for enhancing immunity, which contains *Pediococcus inopinatus*, a culture thereof, a lysate thereof, a pulverization product thereof, a fermentation product thereof or an extract thereof. It is well known that the lactic acid bacteria in the genus *Pediococcus* have probiotic effect and immune-enhancing effect.

In addition, the present disclosure provides a food composition for improving memory, improving cognitive ability, improving muscle power or improving motor ability, which contains *Pediococcus inopinatus*, a culture thereof, a lysate thereof, a pulverization product thereof, a fermentation product thereof or an extract thereof as an active ingredient.

All the foregoing description about *Pediococcus inopinatus* applies also to the food composition.

In a specific exemplary embodiment, the composition may be a composition containing a *Pediococcus inopinatus* WIKIM27 (accession number KCCM12653P) strain.

In another specific exemplary embodiment, the composition may be a composition containing a live or killed *Pediococcus inopinatus* WIKIM27 strain.

In another specific exemplary embodiment, the composition may be a composition containing a culture, lysate, fermentation product or extract of a *Pediococcus inopinatus* WIKIM27 strain.

In the present disclosure, the "improvement of memory" and "improvement of cognitive ability" refer to the effect of restoring memory lapse, memory disorder or decreased cognitive ability caused by the atrophy of the brain and destruction of brain nerve cells owing to physical fatigue, sleep deprivation, excessive alcohol intake, dementia, etc. by controlling harmful substances that damage the brain nerve cells or regulating neurotransmitters in the brain. The memory refers to the ability of the brain by which information is received, stored, and retrieved when needed.

In the present disclosure, the "improvement of muscle power" and "improvement of motor ability" refer to the effect of improving decline in motor ability caused by weakened muscle power owing to various diseases, aging-associated hormonal change, obesity, drinking, smoking, etc. by regulating energy metabolism. The muscle power refers to the maximum force that muscle can exert at once against some resistance (weight or force), and the motor ability refers to the ability of performing exercise using the muscle power.

When the composition of the present disclosure is used as a food composition, the food composition may be in the form of a functional health food, a condiment, a beverage, a bar, etc. In addition, the food composition containing the strain as an active ingredient may be a beverage such as fermented milk, etc. Therefore, the present disclosure provides a fermentation starter for acid bacteria, which contains *Pediococcus inopinatus* or a culture thereof.

The food composition of the present disclosure may be prepared using a sitologically suitable and physiologically acceptable adjuvant in addition to the active ingredient. The adjuvant may include an excipient, a disintegrant, a sweetener, a binder, a coating agent, a swelling agent, a lubricant, a glidant, a flavorant, etc.

The food composition may be formulated into a pharmaceutical composition for administration by adding one or more sitologically acceptable carrier in addition to the active ingredient described above.

For example, for formulation into a tablet or a capsule, the active ingredient may be used in combination with an oral, nontoxic, pharmaceutically acceptable inert carrier such as ethanol, glycerol, water, etc. And, if desired or necessary, a suitable binder, lubricant, disintegrant or coloring agent may also be included. The suitable binder includes a natural sugar such as starch, gelatin, glucose or β-lactose, a corn sweetener, a natural or synthetic gum such as acacia, tragacanth or sodium oleate, sodium stearate, magnesium stearate, sodium benzoate, sodium acetate, sodium chloride, etc., although not being limited thereto. The disintegrant includes starch, methyl cellulose, agar, bentonite, xanthan gum, etc., although not being limited thereto. As an acceptable pharmaceutical carrier in a composition formulated into a liquid solution, one or more ingredient of saline, sterile water, Ringer's solution, buffered saline, albumin injection solution, dextrose solution, maltodextrin solution, glycerol and ethanol, which are sterilized and suitable for the living body, may be mixed. Other conventional additives such as an antioxidant, a buffer, a bacteriostat, etc. may be added, if necessary. In addition, a diluent, a dispersant, a surfactant, a binder or a lubricant may be added additionally for formulation into an injectable formulation such as an aqueous solution, a suspension, an emulsion, etc., a pill, a capsule, a granule or a tablet.

The food composition according to the present disclosure may be added to various foods. The foods to which the composition of the present disclosure can be added include, for example, beverages, vitamin complexes, dietary supplements, etc.

The food composition of the present disclosure may contain ingredients commonly added when preparing foods, for example, a protein, a carbohydrate, a fat, a nutrient, a flavoring agent and a flavorant. Examples of the carbohydrate include common sugars such as a monosaccharide, e.g., glucose, fructose, etc., a disaccharide, e.g., maltose, sucrose, oligosaccharides, etc., a polysaccharide, e.g., dextrin, cyclodextrin, etc. and sugar alcohols such as xylitol, sorbitol, erythritol, etc. As the flavorant, a natural flavorant (thaumatin, stevia extract [e.g., rebaudioside A, glycyrrhizin, etc.]) or a synthetic flavorant (saccharin, aspartame, etc.) may be used. For example, when the food composition of the present disclosure is prepared into a drink or a beverage, citric acid, fructose syrup, sugar, glucose, acetic acid, malic acid, fruit juice, plant extracts, etc. may be further contained.

In addition, the present disclosure provides a pharmaceutical composition for preventing or treating a neurodegenerative disease, which contains *Pediococcus inopinatus*, a culture thereof, a lysate thereof, a pulverization product thereof, a fermentation product thereof or an extract thereof as an active ingredient.

In a specific exemplary embodiment, the composition may be a composition containing a *Pediococcus inopinatus* WIKIM27 (accession number KCCM12653P) strain.

In another specific exemplary embodiment, the composition may be a composition containing a live or killed *Pediococcus inopinatus* WIKIM27 strain.

In another specific exemplary embodiment, the composition may be a composition containing a culture, lysate, fermentation product or extract of a *Pediococcus inopinatus* WIKIM27 strain.

In addition, the present disclosure provides a method for treating a neurodegenerative disease, which includes administering a therapeutically effective amount of *Pediococcus inopinatus*, a culture thereof, a lysate thereof, a pulverization product thereof, a fermentation product thereof or an extract thereof to a subject in need thereof.

The term "subject" used herein refers to a mammal which is the subject of treatment, observation or experiment, specifically human or an animal in need of prevention and/or treatment of a neurodegenerative disease.

In addition, the "neurodegenerative disease" may be one or more diseases selected from the group consisting of Parkinson's disease, Alzheimer's disease, Huntington's disease, Lou Gehrig's disease (amyotrophic lateral sclerosis), Creutzfeldt-Jakob disease, stroke, multiple sclerosis, neuroinflammation, learning disorder, cognitive impairment and memory impairment, although not being limited thereto.

In a specific exemplary embodiment, the neurodegenerative disease may be Parkinson's disease.

In an example described below, it was confirmed that neuroinflammation is suppressed by treatment with a *Pediococcus inopinatus* strain. In addition, it was confirmed by administering a *Pediococcus inopinatus* strain directly to a mouse model of Parkinson's disease and conducting rotarod test and grip strength test that the ability of maintaining balance on a rotating rod and grip strength were superior as compared to a negative control group (PBS-ingested group).

That is to say, it was confirmed that the present disclosure can be used for treating neurodegenerative diseases including Parkinson's disease since the *Pediococcus inopinatus* strain alleviates the symptoms of ataxia in a mouse model of Parkinson's disease.

Neuroinflammation is a cause of various neurodegenerative diseases such as Alzheimer's disease, Parkinson's disease, Lou Gehrig's disease (amyotrophic lateral sclerosis), multiple sclerosis, etc. The relationship between neuroinflammation and the onset of neurodegenerative diseases is well known through a number of literatures (*Mol Med Rep.* 2016 April, 13(4): 3391-3396; *J Immunol Res.* 2018 Apr. 16, 2018: 4784268; *Transl Neurodegener.* 2015, 4: 19), and use of neuroinflammation-regulating substances for treatment of neurodegenerative diseases is also known in the art.

The pharmaceutical composition according to the present disclosure may be administered by common methods via intravenous, intraarterial, intramuscular or intrasternal routes.

The pharmaceutical composition of the present disclosure may contain a pharmaceutically acceptable carrier. In the present disclosure, the term "pharmaceutically acceptable carrier" refers to a carrier or a diluent which does not cause an intolerable side effect and allows the active ingredient to retain its biological activity and characteristics. In the present disclosure, the pharmaceutically acceptable carrier may be one or more of saline, sterile water, Ringer's solution, buffered saline, dextrose solution, maltodextrin solution, glycerol and ethanol. If necessary, another common additive such as an antioxidant, a buffer, a bacteriostat, etc. may be added to formulate an injection suitable for injection to a tissue or organ. In addition, it may be formulated into a dried preparation (particularly, a freeze-dried preparation) which can be prepared into an injectable solution by adding an isotonic sterile solution or, if necessary, sterile water or physiological saline. In addition, a target organ-specific antibody or ligand may be bound to the carrier for specific action on a target organ. Suitable preparations known in the art are described in Remington's Pharmaceutical Science (Mack Publishing Company, Easton PA).

In addition, the composition of the present disclosure may specifically further contain a filler, an excipient, a disintegrant, a binder, a glidant, etc. In addition, the composition of the present disclosure may be formulated using a method known in the art such that the active ingredient is released immediately, in a sustained manner or in a delayed manner after being administered into a mammal.

In the present disclosure, "administration" refers to introduction of the composition of the present disclosure to a patient by any suitable method. The composition of the present disclosure may be administered via various oral or parenteral routes that can access the target tissue. It may be administered intraperitoneally, intravenously, intramuscularly, subcutaneously, intradermally, orally, topically, intranasally, intrapulmonarily or intrarectally, although not being limited thereto.

For example, the composition of the present disclosure may be administered by intramuscular, intravenous or intraperitoneal injection for clinical administration.

For injection, the composition may be specifically prepared into a pharmaceutically acceptable buffer such as Hank's solution, Ringer's solution or physiological saline buffer. For transmucosal administration, a non-penetrating agent suitable for penetration into a barrier is used. The non-penetrating agent is generally known in the art.

Preparations for parenteral administration include a sterilized aqueous solution, a nonaqueous solution, a suspension, an emulsion, etc. For the nonaqueous solution or suspension, propylene glycol, polyethylene glycol, vegetable oil such as olive oil, injectable ester such as ethyl oleate, etc. may be used.

In the present disclosure, "effective amount" refers to an amount necessary to delay or completely stop the onset or progression of a particular disease to be treated, and the effective amount of the *Pediococcus inopinatus* WIKIM27 contained in the pharmaceutical composition of the present disclosure means the amount required to achieve the effect of preventing or treating a neurodegenerative disease. Accordingly, the effective amount may be adjusted depending on various factors including the type of a disease, the severity of the disease, the types and contents of other ingredients contained in the composition, the age, body weight, general health condition, sex and diet of a patient, administration time, administration route, treatment period and co-administered drugs. It is obvious to those skilled in the art that a suitable daily dosage can be determined by a prescriber within the proper medical determination range.

For the objectives of the present disclosure, it is preferred that a specific therapeutically effective amount for a particular patient varies depending on various factors including the type and degree of a reaction to be achieved, the specific composition in which other ingredients may be used in some cases, the age, body weight, general health condition, sex and diet of a patient, administration time, administration route, the excretion rate of the composition, treatment period, co-administered drugs and similar factors well known in the art.

In the present disclosure, "treatment" refers to an approach to obtain beneficial or desirable clinical outcomes. For the purposes of the present disclosure, the beneficial or desirable clinical outcomes include, but are not limited to, alleviation of symptoms, diminishment of the extent of a disease, stabilization of the disease state (i.e., prevention of worsening), delay or slowing of disease progression, amelioration or temporary palliation of the disease state, and remission (whether partial or total), whether detectable or undetectable. In addition, the "treatment" may mean prolonging survival rate as compared to the expected survival rate when the treatment is not given. The "treatment" refers to both therapeutic treatment and prophylactic treatment. The treatment includes not only the prevention of a disorder but also the treatment required for a disorder that has occurred already. The "palliation" of a disease means diminishing the extent of a disease state and/or undesirable clinical symptoms and/or slowing or extending the time course of disease progression as compared to when the treatment is not given.

The present disclosure also provides a feed additive or a feed containing *Pediococcus inopinatus*, a culture thereof, a lysate thereof, a pulverization product thereof, a fermentation product thereof or an extract thereof as an active ingredient.

When used as a feed additive, the composition may be prepared into a 20-90% concentrate, a powder or a granule. The feed additive may further contain one or more of an organic acid such as citric acid, fumaric acid, adipic acid, lactic acid, malic acid, etc. a phosphate such as sodium phosphate, potassium phosphate, an acid pyrophosphate, a polyphosphate, etc., or a natural antioxidant such as polyphenol, catechin, α-tocopherol, rosemary extract, vitamin C, green tea extract, licorice extract, chitosan, tannic acid, phytic acid, etc. When used as a feed, the composition may be prepared into a common feed form and may further contain common feed ingredients.

The feed additive and feed may further contain grains, e.g., pulverized or crushed wheat, oats, barley, corn and rice; vegetable protein feeds, e.g., feeds with rape, bean and sunflower as main ingredients; animal protein feeds, e.g., blood meal, meat meal, bone meal and fish meal; sugars and dairy products, e.g., various dried milk and dried products composed of whey powder, etc. In addition, it may further contain a nutritional supplement, an agent for improving digestion and absorption, an agent for promoting growth, etc.

The feed additive may be administered to an animal either alone or in combination with another feed additive in an edible carrier. In addition, the feed additive may be orally administered to an animal easily as a top dressing, as being directly mixed with an animal feed, or separately from the feed. When the feed additive is administered separately from the animal feed, it may be prepared into a formulation for immediate release or sustained release in combination with a pharmaceutically acceptable edible carrier as well known in the art. The edible carrier may be a solid or a liquid, e.g., cornstarch, lactose, sucrose, soy flake, peanut oil, olive oil, sesame oil or propylene glycol. When a solid carrier is used, the feed additive may be in the form of a tablet, a capsule, a powder, a troche, a lozenge or a finely dispersed top dressing. When a liquid carrier is used, the feed additive may be in the form of a soft gelatin capsule, a syrup, a suspension, an emulsion or a solution.

In addition, the feed additive and the feed may contain an adjuvant, e.g., a preservative, a stabilizer, a wetting agent, an emulsifier, a solubilizer, etc. The feed additive may be added to animal feed by dipping, spraying or mixing.

The feed or feed additive of the present disclosure may be applied to the diet of various animals including mammals, poultry and fish.

The mammal may be a pet (e.g., dog or cat) as well as pig, cow, sheep, goat and a laboratory rodent. The poultry may be chicken, turkey, duck, goose, pheasant, quail, etc. And, the fish may be trout, etc., although not being limited thereto.

The feed or feed additive of the present disclosure may be applied to an animal diet for enhancing the growth, immunity, etc. of animals.

In addition, the feed or feed additive of the present disclosure may be used to improve memory, cognitive ability, muscle power or motor ability of an animal or to prevent, ameliorate or treat a neurodegenerative disease.

The composition according to the present disclosure may contain the *Pediococcus inopinatus* strain in an amount of about $10^6$-$10^{12}$ CFU/mL, e.g., $10^7$-$10^{11}$ CFU/mL or $10^8$-$10^{10}$ CFU/mL, based on a single dose. Specifically, the strain may be administered in live state, and may be killed or attenuated prior to ingestion. In addition, it may further pass through a pasteurization process of heating. The amount of the strain necessary for providing the minimum effect and the recommended daily intake may be generally about $10^6$-$10^{12}$ CFU/mL, e.g., $10^7$-$10^{11}$ CFU/mL or $10^8$-$10^{10}$ CFU/mL, although it can vary depending on the physical or health condition of the recipient.

The advantages and features of the present disclosure and methods for achieving them will become more apparent by the examples descried below. However, the present disclosure is not limited by the examples described below but may be embodied in various other forms. The examples are merely provided such that the disclosure of the present disclosure is complete and those having ordinary knowledge in the art to which the present disclosure belongs can fully understand the scope of the present disclosure. The present disclosure is defined by the appended claims only.

Advantageous Effects

Since a *Pediococcus inopinatus* strain according to the present disclosure not only has an effect of suppressing neuroinflammation but also can improve the symptoms of ataxia in an animal model of Parkinson's disease, it can be used for preventing, alleviating and treating various neurodegenerative diseases including Parkinson's.

Deposits

The Deposit with Korean Culture Center of Microorganisms, under deposit accession number KCCM12653P was made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BEST MODE

Hereinafter, the present disclosure is described in detail through examples. The following examples merely illustrate the present disclosure, and the scope of the present disclosure is not limited by the examples.

EXAMPLES

Example 1: Preparation of *Pediococcus inopinatus* Strain

A *Pediococcus inopinatus* WIKIM27 strain, which is derived from kimchi and is deposited in the Korea Culture Center of Microorganisms with the accession number KCCM12653P, was used for experiment. After culturing the *Pediococcus inopinatus* WIKIM27 strain in an MRS medium at 30° C. for 24 hours, the cells were centrifuged at 8,000 rpm for 5 minutes and the remaining medium was removed by rinsing with PBS. After inoculating the cells into DMEM (Dulbecco's modified Eagle's medium, HyClone, USA) medium at a density of $1\times10^9$ CFU/mL and culturing at 30° C. for 24 hours, the cells were removed by centrifuging at 8,000 rpm for 5 minutes. After adjusting the pH of the supernatant to 7.2, it was filtered through a syringe filter (pore size: 0.22 µm).

Example 2: Primary Culture of Neuroglial Cells

After disinfecting the scalp of a 2-day-old Sprague-Dawley rat with alcohol, the cerebrum was taken out immediately without damaging. The extracted cerebrum was immersed in cold HBSS (Hank's balanced salt solution) and only the cerebral cortex was separated under a dissecting microscope. After preparing a single cell suspension using a Pasteur pipette, the cells were cultured for 10 days. Neuroglial cells were cultured in a 5% $CO_2$ incubator at 37° C. using DMEM containing 10% fetal bovine serum (HyClone, USA), 10% horse serum (HyClone, USA) and 1% penicillin/streptomycin (GIBCO, USA).

Figure 1:
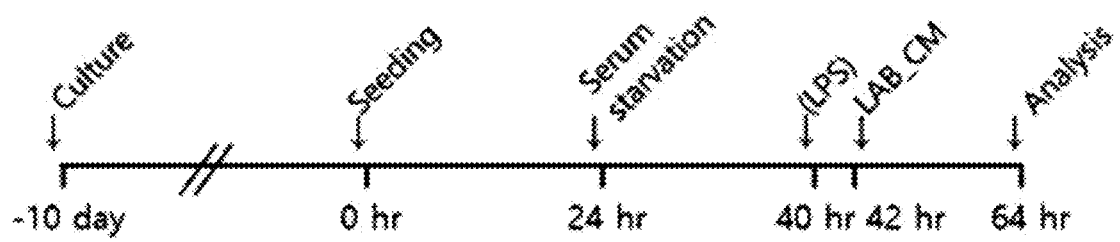
FIG. 1 schematically shows an experimental procedure for investigating the neuroinflammation-suppressing effect of a *Pediococcus inopinatus* WIKIM27 strain of the present disclosure.

Example 3: Investigation of Neuroinflammation-Suppressing Effect of *Pediococcus inopinatus* Strain In order to investigate the neuroinflammation-suppressing effect of the *Pediococcus inopinatus* WIKIM27 strain prepared in Example 1, inflammation was induced in neuroglial cells with LPS (lipopolysaccharide) and the cells were treated with the culture of WIKIM27. After seeding the neuroglial cells onto a 24-well plate at a concentration of $1.0\times10^5$ cells/mL and replacing with a serum-free medium 24 hours later, the cells were treated with 100 ng/mL LPS 16 hours later. Two hours after the treatment with LPS, the cells were treated with the culture of WIKIM27 with a volume of ⅕ of that of the neuroglial cell medium. The experimental procedure is schematically shown in FIG. 1. A *Weissella cibaria* WIKIM28 (accession number KFCC11625P) strain and a *Lactobacillus sakei* WIKIM30 (accession number KFCC11618P) strain were used as control groups.

Figure 2:
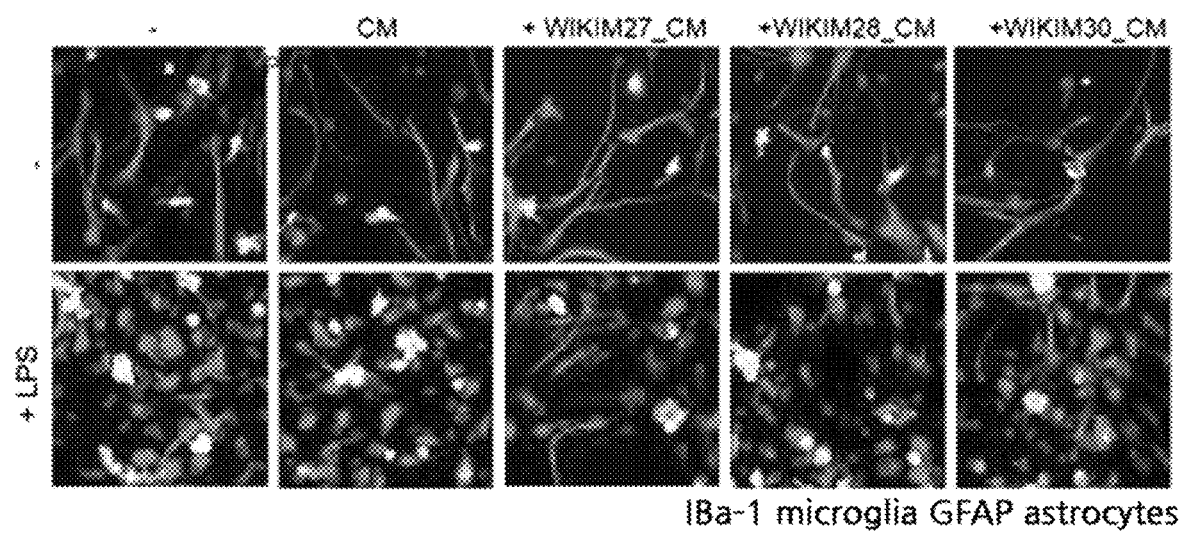
FIG. 2 shows a result of observing the result of treating neuroglial cells in which inflammation is induced by LPS with a *Pediococcus inopinatus* WIKIM27 strain of the present disclosure through immunofluorescence staining.
Figure 3:
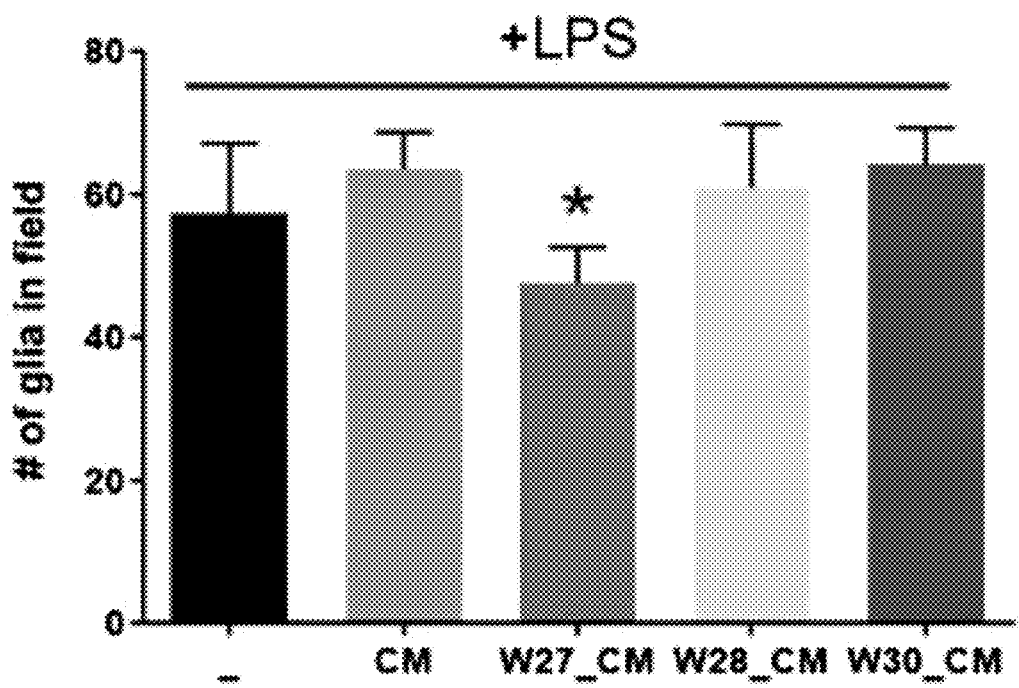
FIG. 3 shows a result of treating neuroglial cells in which inflammation is induced by LPS with a *Pediococcus inopinatus* WIKIM27 strain of the present disclosure.

As seen from FIGS. 2 and 3, it was confirmed through immunohistochemical analysis that the WIKIM27 treatment group (W27_CM) showed significantly decreased activity of neuroglial cells (microglia and astrocytes) despite the induction of neuroinflammation with LPS. As selective markers for microglia and astrocytes, Iba-1 (ionized calcium-binding adapter molecule 1) and GFAP (glial fibrillary acidic protein) were used, respectively. It was confirmed that the culture of the WIKIM27 strain alleviates neuroinflammation.

Example 4: Preparation and Administration of *Pediococcus inopinatus* Strain After culturing a *Pediococcus inopinatus* WIKIM27 strain in MRS medium at 30° C. for 24 hours, the cells were centrifuged at 8,000 rpm for 5 minutes and the remaining medium was removed by rinsing with PBS. $1\times10^{10}$ CFU/mL of cells were quantitated using PBS. 0.2 mL ($1\times10^9$ CFU) was orally administered to an experimental animal 5 times a week. Sterilized PBS was administered to negative and positive control groups.

Example 5: Investigation of Treatment of Animal Model with *Pediococcus inopinatus* Strain on Prevention and Treatment of Parkinson's Disease In order to investigate the therapeutic effect of the *Pediococcus inopinatus* WIKIM27 strain prepared in Example 1 on Parkinson's disease, rotarod test and grip strength test were conducted for a mouse model of Parkinson's disease. The mouse model of Parkinson's disease was established by accustoming 8-week-old male mice (C57BL/6) in a laboratory room for a week, orally administering the *Pediococcus inopinatus* WIKIM27 strain for 30 days and then inducing Parkinson's disease by intraperitoneally injecting MPTP (1-methyl-4-phenyl-1,2,3,6-tetrahydropyridine, 30 mg/kg, once a day for 5 days). Naive stands for a non-treatment group, MPTP a negative control group, Selegiline a positive control group. Selegiline is an inhibitor of MAO-B, which is a neuroprotective material, and was orally administered (3 mg/kg) 3 days before the MPTP injection.

1) Rotarod Test

Rotarod test was performed by measuring riding time on a rotarod consisting of a base platform and a rotating rod with a non-slippery surface. Evaluation was conducted at 30 minutes after training the mouse at a speed of 4 rpm for 2 minutes for accustomation. The rotation speed was increased from 4 rpm up to 40 rpm, with an acceleration paradigm of 1 rpm per 8 seconds, and the maximum rotation speed was maintained at 40 rpm for 300 seconds.

Figure 4:
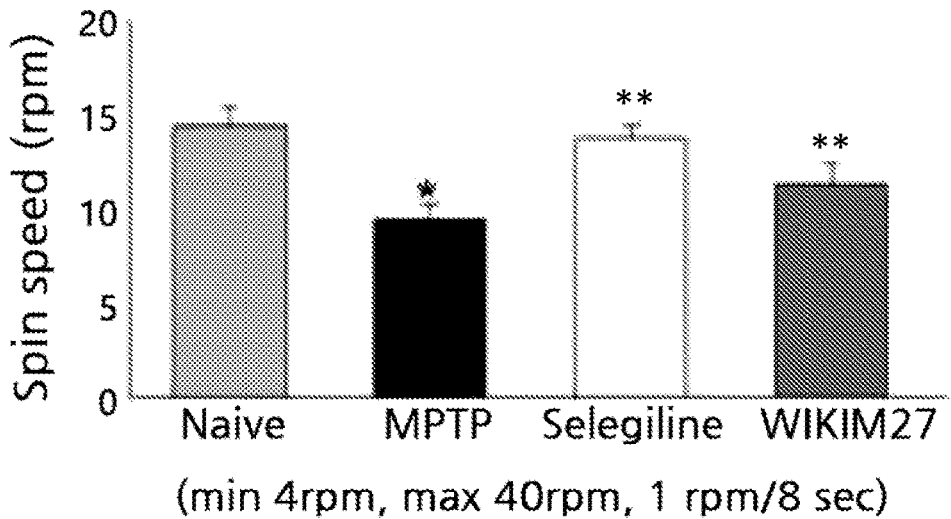
FIG. 4 shows a result of orally administering a *Pediococcus inopinatus* WIKIM27 strain of the present disclosure to a mouse model of Parkinson's disease and then evaluating the motor ability of the mouse using a rotarod.

As a result (FIG. 4), the negative control group treated with PBS maintained balance at a speed of 7.7 rpm on average, whereas the test group to which the *Pediococcus inopinatus* WIKIM27 strain was administered orally could maintain balance at a speed of 10.6 rpm on average.

2) Grip Strength Test

Grip strength test was performed by measuring the grip strength of the paw of the mice with a grip strength meter. The grip strength of the paw of the mice was measured 5 times and the highest 3 values were averaged.

Figure 5:
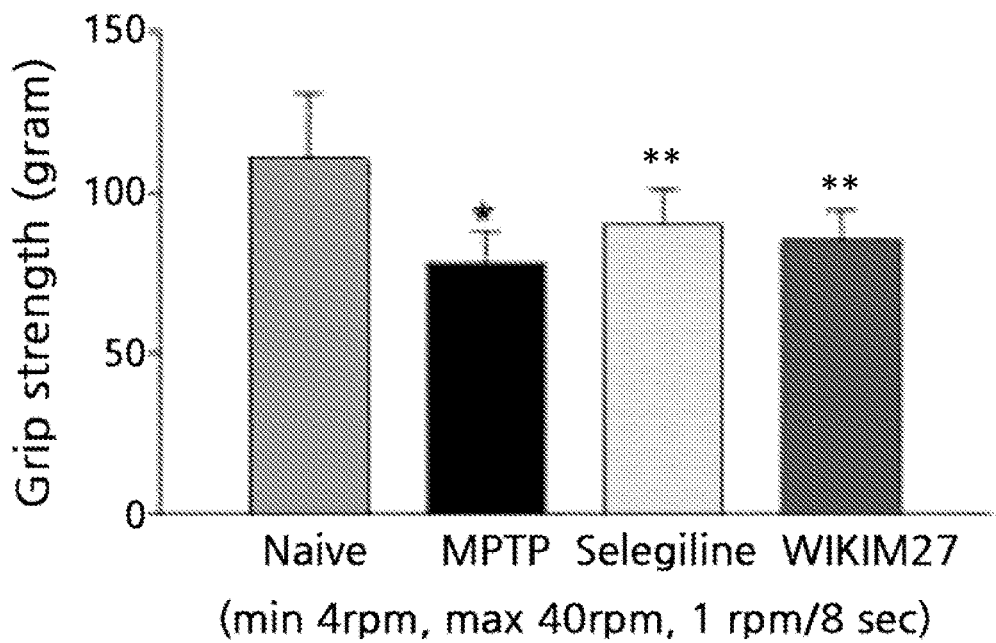
FIG. 5 shows a result of orally administering a *Pediococcus inopinatus* WIKIM27 strain of the present disclosure to a mouse model of Parkinson's disease and then evaluating the grip strength of the mouse.

As a result (FIG. 5), the negative control group showed a paw grip strength of 77.78 gram, whereas the test group to which the *Pediococcus inopinatus* WIKIM27 strain was administered orally showed a very high grip strength of 85.79 gram as compared to the negative control group.

That is to say, since the ingestion of the *Pediococcus inopinatus* WIKIM27 strain resulted in better results of rotarod and grip strength tests in the mouse model of Parkinson's disease as compared to the negative control group, it was confirmed that the symptoms of ataxia in the mouse model of Parkinson's disease can be improved significantly ($p<0.05$).

We claim:

1. A method for treating a neurodegenerative disease, comprising administering a composition comprising a therapeutically effective amount of *Pediococcus inopinatus*, or a culture thereof to a subject in need thereof,
    wherein the *Pediococcus inopinatus* is *Pediococcus inopinatus* WIKIM27 deposited with an accession number KCCM12653P.

2. The method according to claim 1, wherein the composition is a pharmaceutical composition, a food composition or a feed additive composition.

3. The method according to claim 1, wherein the neurodegenerative disease is one or more selected from the group consisting of Parkinson's disease, Alzheimer's disease, Huntington's disease, Lou Gehrig's disease (amyotrophic lateral sclerosis), Creutzfeldt-Jakob disease, stroke, multiple sclerosis, neuroinflammation, learning disorder, cognitive impairment and memory impairment.

4. The method according to claim 2, wherein the pharmaceutical composition is orally administered.

5. The method according to claim 2, wherein the pharmaceutical composition comprises $1 \times 10^6$ CFU/mL to $1 \times 10^{12}$ CFU/mL of *Pediococcus inopinatus*.

6. The method according to claim 2, wherein the pharmaceutical composition treats the symptoms of ataxia in a subject having Parkinson's disease.

7. The method according to claim 2, wherein the food is a functional health food.

8. The method according to claim 2, wherein the food is a beverage, a bar or a fermented milk.

9. The method of claim 1, wherein the neurodegenerative disease is Parkinson's disease.

\* \* \* \* \*